(12) United States Patent
Ducharme et al.

(10) Patent No.: US 11,337,818 B2
(45) Date of Patent: May 24, 2022

(54) SYSTEMS AND METHODS FOR FUSION OF ANATOMICAL JOINTS

(71) Applicants: Dustin Ducharme, Littleton, CO (US); Kevin Stamp, Sheffield (GB); Geoff Lai, Lakewood, CO (US)

(72) Inventors: Dustin Ducharme, Littleton, CO (US); Kevin Stamp, Sheffield (GB); Geoff Lai, Lakewood, CO (US)

(73) Assignee: Ortho Solutions Inc., Littleton, CO (US)

( * ) Notice: Subject to any disclaimer, the term of this patent is extended or adjusted under 35 U.S.C. 154(b) by 0 days.

(21) Appl. No.: 16/424,050

(22) Filed: May 28, 2019

(65) Prior Publication Data

US 2019/0358039 A1 Nov. 28, 2019

Related U.S. Application Data

(60) Provisional application No. 62/676,635, filed on May 25, 2018.

(51) Int. Cl.
| | |
|---|---|
| *A61B 17/80* | (2006.01) |
| *A61F 2/30* | (2006.01) |
| *A61F 2/42* | (2006.01) |
| *A61B 17/86* | (2006.01) |

(52) U.S. Cl.
CPC ............ *A61F 2/30* (2013.01); *A61B 17/8014* (2013.01); *A61B 17/8047* (2013.01); *A61B 17/8057* (2013.01); *A61B 17/8061* (2013.01); *A61B 17/863* (2013.01); *A61F 2/4202* (2013.01); *A61F 2002/30622* (2013.01); *A61F 2002/4233* (2013.01)

(58) Field of Classification Search
CPC . A61B 17/80; A61B 17/8061; A61B 17/8014; A61B 17/8033; A61B 17/7013; A61F 2/4202; A61F 2002/30622; A61F 2002/4233
See application file for complete search history.

(56) References Cited

U.S. PATENT DOCUMENTS

| | | |
|---|---|---|
| 5,954,722 A | 9/1999 | Bono |
| 6,142,998 A | 11/2000 | Smith et al. |
| 7,406,775 B2 | 8/2008 | Funk et al. |

(Continued)

OTHER PUBLICATIONS

International Preliminary Report on Patentability from related PCT/US2019/034212, dated Dec. 1, 2020. 16 pages.

(Continued)

*Primary Examiner* — Christopher D. Prone
(74) *Attorney, Agent, or Firm* — FisherBroyles LLP; Ian R. Walsworth

(57) ABSTRACT

The present disclosure relates to improved plate and screw systems for use in fusion and other surgical procedures, which improve the ability to effectively affix adjacent bodies without gapping or experiencing loss of compression over time. The systems include plates having armatures configured to receive bushings, the bushings configured to pivot and rotate and thereby permit a greater degree of orientation of corresponding screws placed through the bushings. In embodiments, the bushings comprise anti-rotation elements which lock the bushings in a desired orientation. Methods for use of the components described herein are also disclosed.

15 Claims, 16 Drawing Sheets

(56) References Cited

U.S. PATENT DOCUMENTS

| | | | |
|---|---|---|---|
| 9,545,276 B2 * | 1/2017 | Buchanan | A61B 17/8061 |
| 9,861,405 B2 | 1/2018 | Day et al. | |
| 2004/0210220 A1 | 10/2004 | Tornier | |
| 2005/0004574 A1 | 6/2005 | Muckter | |
| 2008/0119895 A1 | 5/2008 | Manceau | |
| 2008/0300637 A1 * | 12/2008 | Austin | A61B 17/8605 |
| | | | 606/290 |
| 2013/0006311 A1 | 1/2013 | Castaneda et al. | |
| 2013/0190575 A1 | 7/2013 | Mast et al. | |
| 2014/0277176 A1 | 9/2014 | Buchanan et al. | |
| 2015/0045837 A1 | 2/2015 | Parekh et al. | |
| 2015/0112395 A1 | 4/2015 | Day et al. | |
| 2016/0066969 A1 | 3/2016 | Reuter | |
| 2016/0354128 A1 | 12/2016 | Jeng et al. | |
| 2016/0367300 A1 * | 12/2016 | Caldarella | A61B 17/808 |

OTHER PUBLICATIONS

International Search Report from related PCT/US2019/034212, dated Sep. 30, 2019. 5 pages.

* cited by examiner

SYSTEMS AND METHODS FOR FUSION OF ANATOMICAL JOINTS

CROSS-REFERENCE TO RELATED APPLICATIONS

This application claims the benefit of U.S. Provisional Patent Application Ser. No. 62/676,635, filed May 25, 2018, the entirety of which is incorporated by reference herein.

FIELD

The present disclosure generally relates to the field of medical devices, and more specifically to systems for use in fusion and other surgical procedures. Methods for using the foregoing devices are also disclosed herein.

BACKGROUND

Surgeries on joints in the human body often require fixation of two or more adjacent bodies, including where those bodies are intended for post-fusion articulation. A "fusion" is a commonly used surgical procedure where two or more adjacent bodies are joined together. Fusion also commonly involves the use of plates, screws and other devices into a small surgical site. Given the size of the plates, screws and other devices used in these types of surgeries, the complexities of the associated surgical procedures, as well as other factors, it is often challenging to provide a device or implant that is adequate for use in a successful fusion surgery, and that otherwise meets the surgical plan. Such surgical procedures often require introduction of additional tools to prepare the surgical site, including drills, drill guides, debridement tools, irrigation devices, clamps, pins, cannula and other tools.

Many prior art plates and screw systems suffer from significant disadvantages, such as large footprint, excessive prominence, poor placement, inaccurate trajectory, poor stability/flexibility, difficulty in handling, loss of permanent fixation/subsidence, impaired visibility and other disadvantages. These disadvantages often result in a relatively high rate of failure or discomfort, particularly when applied to the foot or ankle of a patient. Further, many plate systems are designed for only a specific type of type, size or shape of screw, and therefore limit their applicability.

Other plating systems do not provide flexibility with respect to orientation of the plate and/or screws, limiting their applicability and causing discomfort/pain to the patient. For instance, many plates do not provide a wide degree of orientation of a screw placed through the bore(s) of the plate. This in turn creates difficulty when attempting shallow angles of penetration through the plate and patient's boney anatomy. Further problems exist in prior art plating systems that comprise multiple bores and do not sufficiently protect against intersecting screw trajectories.

There is also an increasing benefit of performing fusion and other procedures by a minimally-invasive surgery ("MIS"). During a MIS procedure, a less destructive/invasive approach to the patient is carried out, which may involve the use of much smaller retractors than an "open" procedure, and which in turn limit the potential damage to intervening anatomical landmarks. Plates and screws must meet additional criteria for use in MIS procedures, which are often unmet by existing systems.

It would therefore be advantageous to provide a system and method for achieving fusion that significantly reduces, if not eliminates, the shortcoming, problems and risks noted above. Other advantages over the prior art will become known upon review of the Summary and Detailed Description sections herein.

SUMMARY

According to various embodiments presented herein, the present disclosure describes improved plate and screw systems for use in fusion and other surgical procedures. More specifically, the systems described below greatly improve the ability to effectively affix adjacent bodies without gapping or experiencing loss of compression over time.

In one aspect of the present disclosure, the systems and methods provide a plate comprising one or more armatures for placement of screws in a converging arrangement, which in turn promotes the objectives described herein.

In another aspect of the present disclosure, the systems and methods permit components to be introduced during a minimally-invasive surgical procedure.

In yet another aspect of the present disclosure, the plate comprises one or more retaining collars for securing a compression-type or polyaxial-type screw.

In yet another aspect of the present disclosure, the collars are adapted to receive a bushing for adjusting orientation of a screw or equivalent fastener extending therethrough. In one embodiment, the bushing is threaded. In another embodiment, the bushing is dual-threaded. In yet another embodiment, the bushing comprises a cam, a slope or equivalently-shaped surface to provide an orientation to a screw or equivalent fastener inserted therethrough.

In yet another aspect of the present disclosure, the armature(s) and/or collar(s) described herein provide flexible orientation of a screw or equivalent fastener passing therethrough, while maintaining adequate spacing among the various trajectories achievable with the system.

In yet another aspect of the present disclosure, the systems and methods provide for insertion of multiple screws or equivalent fasteners in a plane(s) offset by about 90 degrees. In this manner, the systems and methods achieve greater compression and avoid gapping and other problems associated with prior art systems and methods.

In one embodiment, the system comprises: a plate having one or more armatures, each of the one or more armatures offset from the longitudinal or x-axis of the plate; the one or more armatures comprising a recess having an inner surface; a bushing having an outer surface complementary to the inner surface of the recess and configured to be received by and retained by the recess, wherein the bushing further comprises a through hole accessible via the recess when the bushing is retained therein; a screw comprising a threaded portion, a non-threaded portion and a screw head complementary to the through hole of the bushing, wherein the threaded and non-threaded portions of the screw pass through the through hole of the bushing, wherein the screw head is captured by the through hole of the bushing, and wherein rotation of the screw once the screw head is captured by the bushing rotates the bushing relative to the recess; and wherein further rotation of the bushing secures the position of the bushing relative to the recess, thereby locking the bushing and the screw in a fixed orientation relative to the plate.

According to another embodiment, the system comprises: a thin plate having a longitudinal or x-axis and first and second medial sides, the plate comprising one or more generally cylindrical bores extending therethrough; the plate further comprising two or more armatures extending from the first or second side of the plate; the two or more armatures comprising a recess having an inner surface and a notch located along the inner surface; each of the two or more armatures adapted to receive a bushing configured to fit within the recess of the corresponding armature and having an outer profile that is complementary to the inner surface of the recess within which it is received, the bushings permitted to pivot or rotate within the recesses; each bushing having at least one outwardly-extending protrusion; and wherein the bushing is prevented from pivoting or rotating once the outwardly-extending protrusion configured to engage the notch along the inner surface of the recess.

In yet another embodiment, the system comprises: a plate comprising one or more armatures, each of the one or more armatures offset from and extending about 90 degrees to the x-axis of the plate; the plate comprising at least one bore configured to receive a first screw oriented in a z-axis relative to the plate; the one or more armatures having a distal (or terminal) end and comprising a recess located at a distal end of the armature and having an inner surface; a bushing having an outer surface complementary to the inner surface of the recess and configured to be selectively received by and retained by the recess, wherein the bushing further comprises a through hole accessible via the recess when the bushing is retained therein; a second screw comprising a threaded portion, a non-threaded portion and a screw head having an outer surface complementary to the through hole of the bushing, wherein the threaded and non-threaded portions of the second screw pass through the through hole of the bushing in use, and wherein the outer surface of the screw head is configured to be retained within the through hole of the bushing, and wherein the second screw is oriented in the direction of and normal to the orientation of the first screw.

In yet another embodiment, the present disclosure relates to an assembly comprising:

a thin plate having first and second sides, the thin plate comprising one or more cylindrical bores extending therethrough;

the thin plate further comprising two or more armatures extending from the first or second side of the plate;

the two or more armatures comprising a recess having an inner surface and a notch located along the inner surface;

each of the two or more armatures adapted to receive a bushing configured to fit within the recess of the corresponding armature and having an outer profile that is complementary to the inner surface of the recess within which it is received, the bushings permitted to pivot or rotate within the recesses;

each bushing having at least one outwardly-extending protrusion; and wherein the bushing is prevented from pivoting or rotating once the outwardly-extending protrusion engages the notch along the inner surface of the recess. In yet another embodiment, the disclosure relates to an orthopedic implant system comprising a spanning link having a longitudinal axis in the x direction and having a first spanning link fastener with a first spanning link fastener axis which forms an angle relative to the spanning link longitudinal axis of from 80 degrees to 100 degrees, and a first leg link extending away in the y and z direction from the of the spanning link longitudinal axis and having a first leg link fastener aperture that receives a first leg link fastener which has a first leg link fastener axis that extends away from the first leg link fastener aperture in the direction of but not intersecting the first spanning link fastener axis.

In yet another embodiment, the disclosure relates to an orthopedic implant system, comprising:

a spanning link having a longitudinal axis in the x direction and having a first spanning link fastener aperture that receives a first spanning link fastener with a first spanning link fastener axis which forms an angle relative to the spanning link longitudinal axis of from 80 degrees to 100 degrees and having a second spanning link fastener aperture that receives a second spanning link fastener with a second spanning link fastener axis which forms an angle relative to the spanning link longitudinal axis of from 80 degrees to 100 degrees and the spanning link defining a fusion area located between the first spanning link fastener and the second spanning link fastener;

a first leg link extending away in the y-z direction having a first leg link length from the spanning link longitudinal axis and having a first leg link fastener aperture which receives a first leg link fastener which has a first leg link fastener axis that extends away from the first leg link fastener aperture in the direction of the fusion area;

a second leg link extending away in the y-z direction having a second leg link length from the spanning link longitudinal axis and having a second leg link fastener aperture which receives a second leg link fastener which has a second leg link fastener axis that extends away from the second leg link fastener aperture in the direction of the fusion area; and wherein the first leg link fastener axis and the second leg link fastener axis converge toward each other, but do not intersect.

In yet another embodiment, the disclosure relates to an orthopedic implant system having an outline consisting of a single spanning link that extends from 15 to 60 mm along a long axis and has two opposing terminal ends joined across a short axis at a width of 2 to 5 mm by two opposing long sides, and each of the terminal ends include a through aperture each of which receives a cross screw and at least one the cross screws being a polyaxial compression screw, and wherein the cross screw axes are in differing planes and form an X-shape but wherein the cross screws do not contact each other.

In yet another embodiment, the disclosure relates to an implant which comprises a first long curved spanning link having a top surface and a medial line along its length and a first end having a first ear having a first fastener aperture and a second end having a second ear having a second fastener aperture and the long spanning link is fixed at the first end by a first fastener that extends through the first fastener aperture at 90 degrees+/−10 degrees to the medial line of the spanning link and aperture and the long spanning link is fixed at the second end by a second fastener that extends through the second fastener aperture at 90 degrees+/−10 degrees to the medial line of the spanning link, a first leg link and a second leg link each extending away from the medial line of the spanning link and the first leg link and the second leg link each having a terminal aperture for a first and second leg link fastener respectively.

In yet another embodiment, the disclosure relates to an orthopedic implant system having an outline comprising a spanning link that extends from 15 to 60 mm along a long axis and has two opposing terminal ends joined across a short axis at a width of 2 to 5 mm by two opposing long sides and each of the terminal ends that each have a top surface and extend away from the long axis to collectively form a T-shape, and the legs each have an eyelet defining a surface around an aperture in a plane at from 60 to 120 degrees relative to the top surface of the respective leg, and each of which receives a cross screw with at least one being a polyaxial compression screw, and wherein the cross screw axes are in differing planes that form an X-shape but which do not interfere with each other.

In yet another aspect of the present disclosure, a method of using the aforementioned system is disclosed, including but not limited to in a minimally-invasive surgical setting.

The present disclosure has significant benefits across a broad spectrum of endeavors. Particular benefits and improvements over the prior art include: a vastly decreased footprint of plate; lesser prominence of plate and screws; easier to insert/install; availability of MIS/percutaneous applications; appropriate rigidity in an effort to minimize bone resorption; multi-planar fixation; screws inserted in planes offset by about 90 degrees; permitting crossing screw trajectories; avoiding intersecting screw trajectories; permitting converging or diverging screw trajectories; providing a biomechanically superior construct and overall structure; avoiding use of screws of a locking type; permitting a surgeon to hit dorsally and plantarly to minimize gapping; achieve even force distribution; greater compression at the surgical site; and less risk of subsidence.

Potential indications/procedures for which the system and method of the present disclosure are particularly applicable include: Metatarsalphalangeal (MTP) fusions, Calcaneocuboid fusions, Talonavicular fusions, Navicularcueiform fusions, Lapidus (i.e., 1st metatarsal cuneiform fusion, osteotomies of the 1st metatarsal), Ankle fusions and others. In other embodiments, the systems and methods disclosed herein are applicable to joints and/or anatomical features outside the foot and ankle region.

The phrases "at least one," "one or more," and "and/or," as used herein, are open-ended expressions that are both conjunctive and disjunctive in operation. For example, each of the expressions "at least one of A, B and C," "at least one of A, B, or C," "one or more of A, B, and C," "one or more of A, B, or C," and "A, B, and/or C" means A alone, B alone, C alone, A and B together, A and C together, B and C together, or A, B and C together.

Unless otherwise indicated, all numbers expressing quantities, dimensions, conditions, and so forth used in the specification and claims are to be understood as being approximations which may be modified in all instances as required for a particular application of the novel systems and methods described herein. The phrase "about" when used in relation to an angle, conical area or other range expressed in degrees means+/−10 degrees.

It is expressly understood that where the term "patient" has been used to describe the various embodiments of the disclosure, the term should not be construed as limiting in any way. For instance, a patient could be either a human patient or an animal patient, and the systems and methods described herein apply equally to veterinary science as they would to surgical procedures performed on human anatomy. The system and methods described herein therefore have application beyond surgical procedures on the foot and ankle, and the concepts may be applied to other types of "patients" and procedures without departing from the spirit of the present disclosure.

The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials, or acts and the equivalents thereof shall include all those described in the Summary, Brief Description of the Drawings, Detailed Description, Abstract, and Claims themselves.

By way of providing additional context and to further satisfy the written description requirements of 35 U.S.C. § 112, the following are incorporated by reference in their entireties for the express purpose of explaining and further describing the various tools, implants and other apparatus commonly associated with surgical procedures, including MIS procedures: U.S. Pat. No. 6,142,998 to Smith et al.; U.S. Pat. No. 7,406,775 to Funk et al.; and U.S. Pat. No. 9,861,405 to Day et al.

The Summary is neither intended, nor should it be construed, as being representative of the full extent and scope of the present disclosure. Moreover, references made herein to "the present disclosure" or aspects thereof should be understood to mean certain embodiments of the present disclosure and not necessarily be construed as limiting all embodiments to a particular description. The present disclosure is set forth in various levels of detail in the Summary as well as in the attached drawings and the Detailed Description, and no limitation as to the scope of the present disclosure is intended by either the inclusion or non-inclusion of elements or components when describing certain embodiments herein. Additional aspects of the present disclosure will become more apparent from the Detailed Description, particularly when taken together with the drawings.

The above-described benefits, embodiments, and/or characterizations are not necessarily complete or exhaustive, particularly as to the patentable subject matter disclosed herein. Other benefits, embodiments, and/or characterizations of the present disclosure are possible utilizing, alone or in combination, as set forth above and/or described in the accompanying figures and/or in the description herein below.

BRIEF DESCRIPTION OF THE DRAWINGS

The accompanying drawings, which are incorporated herein and constitute a part of the specification, illustrate embodiments of the disclosure, and together with the Summary and the Detailed Description serve to explain the principles of these embodiments. In certain instances, details that are not necessary for an understanding of the disclosure or that render other details difficult to perceive may have been omitted. It should be understood, of course, that the present disclosure is not necessarily limited to the particular embodiments illustrated herein. In the drawings.

The foregoing drawing figures are not necessarily to scale. In certain figures, more or less detail has been shown to streamline the disclosure and/or provide clarity to the illustrations. It is expressly understood that certain embodiments shown in any one of the foregoing drawing figures may comprise other elements shown or described in relation to other embodiments, and that such combinations and sub-combinations are considered within the scope of the present disclosure.

DETAILED DESCRIPTION

It is the Applicant's intent that this specification and the inventions described herein be accorded a breadth in keeping with the scope and spirit of the disclosure and various embodiments disclosed, despite what might appear to be limiting language imposed by certain examples described in detail below. To acquaint persons skilled in the pertinent arts most closely related to the present disclosure, preferred and/or exemplary embodiments are described in detail without attempting to describe all of the various forms and modifications in which the novel apparatus, devices, systems and methods might be embodied. As such, the embodiments described herein are illustrative, and as will become apparent to those skilled in the arts, may be modified in numerous ways within the spirit of the disclosure.

Embodiments of the present disclosure present several advantages over the prior art including, for example, the speed and efficacy of the procedure, the minimally invasive aspects of the procedure, the disposability and/or reusability of components of the system, the ability to introduce tools, instrument and components of the system to a surgical site with minimal risk of damage to the surrounding tissue, lower risk of infection, more optimally placed fasteners, decreased risk of components of the system becoming misaligned or dislodged, and fewer and/or less expensive components required for a particular surgery, among other advantages.

Figure 1:
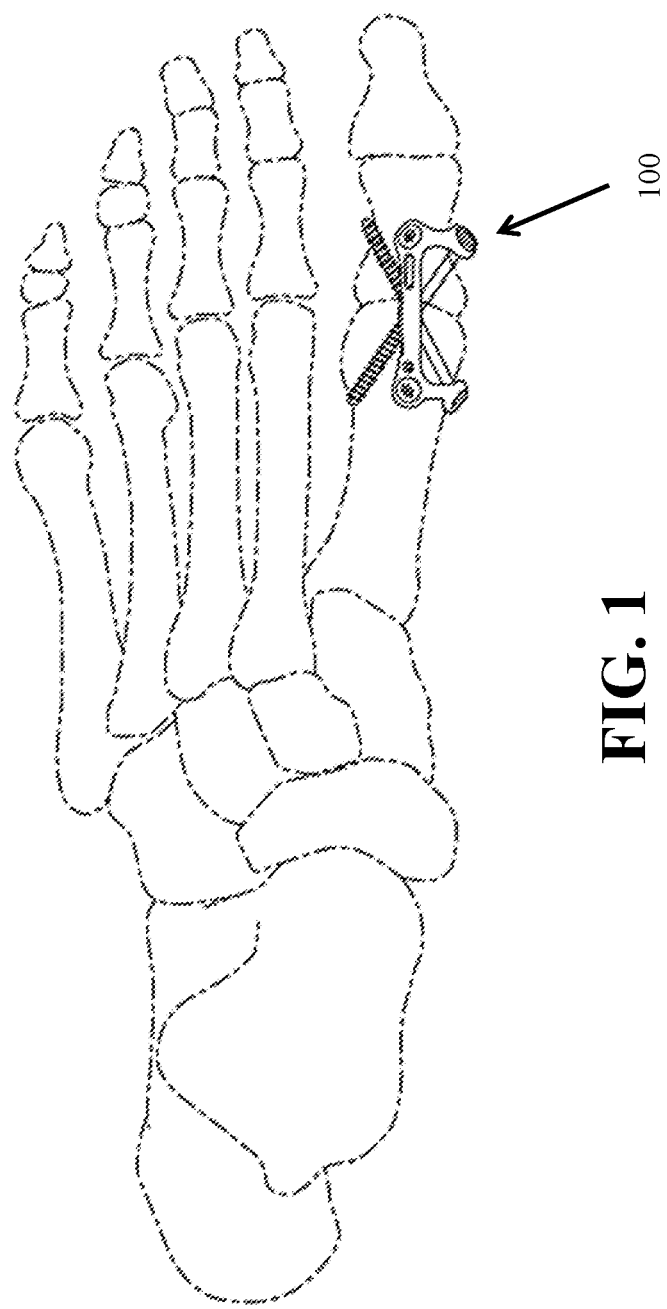
FIG. 1 shows a top perspective view of the system according to an embodiment of the present disclosure.

Referring now to FIGS. 1-16, certain embodiments of the present disclosure are shown. Referring to FIG. 1, the system 100 in varying embodiments is comprised of components well suited for placement and use proximate to the Metatarsophalangeal joint. More particularly, components of the system 100 are adapted to be received against one or more bodies to facilitate, for example, fusion between the one or more bodies. Other procedures for use with the system 100 of the present disclosure include, but are not limited to, Calcaneocuboid fusions, Talonavicular fusions, Navicularcueiform fusions, Lapidus, Ankle fusions and other fusions of the foot and ankle. Details relating to the different components used in these and other procedures are provided below.

Figure 2A:
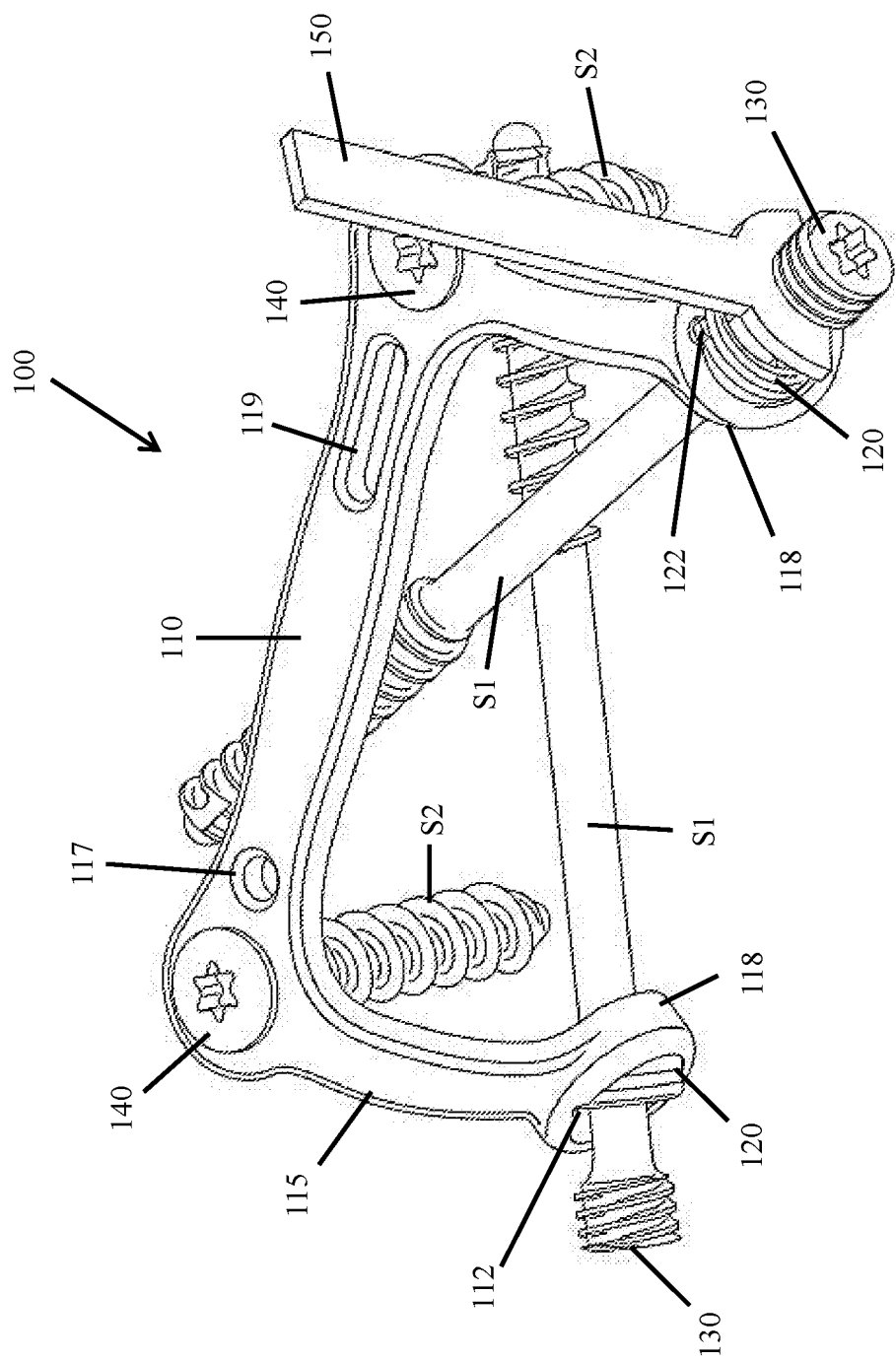
FIG. 2a shows a detailed perspective view of the system of FIG. 1.
Figure 2B:
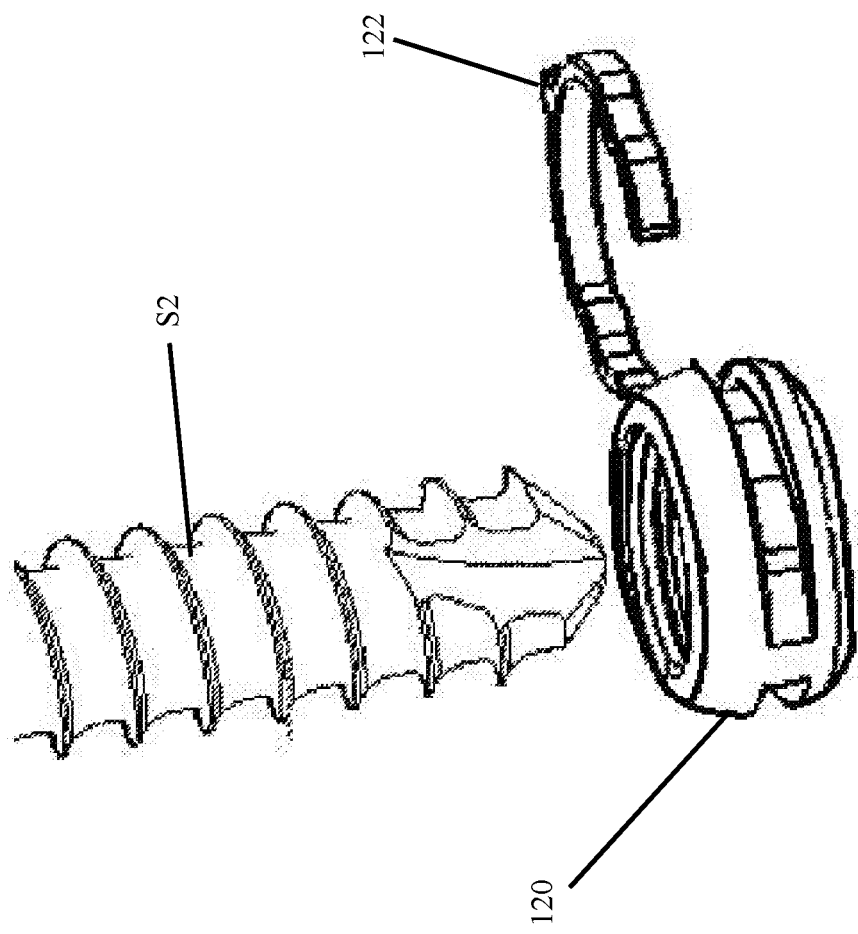
FIG. 2b shows a detailed view of certain components of the system of FIG. 1.

Referring to FIGS. 2a-2b, the system 100 may be comprised of one or more components, and according to one embodiment comprises a plate 110. The plate 110 preferably comprises a central portion and one or more armatures 115. The armatures 115 preferably extend from the central portion of the plate 110 and may be close to perpendicular to the longitudinal or x-axis of the central portion. As shown in FIG. 2, the one or more armatures 115 are preferably arcuate or semi-arcuate in shape as the armatures 115 extend from the central portion of the plate 110. The plate preferably comprises one or more apertures or bores 140, while the one or more armatures 115 preferably comprise a substantially hollow collar 118 for inserting or guiding one or more fasteners, such as a cannulated, cortical or cancellous screw or similar fastener.

The bores 140 of the plate 110 may be cylindrical, circular, elliptical, conical, oval or other shapes, and may be oriented and/or aligned to permit fasteners, such as screws S2 to be inserted in a generally parallel manner, while the collar(s) 118 may be aligned in a manner to permit fixations devices, such as screws S1 to be inserted in a generally converging manner, but without permitting any of the fasteners to intersect when inserted into the adjoining bodies. This provides numerous benefits to the surgeon and the patient, such as orienting fixations devices in three orthogonal planes, as well as the other benefits addressed in the Summary.

To improve flexibility with respect to alignment of screws S1, the collars 118 may be configured to receive a bushing 120. The outer circumference of the bushing 120 may be configured to closely match the interior dimensions of the collar 118, such that the bushing 120 may be received and retained by the collar 118, including in either a threaded or non-threaded engagement. The collar 118 may comprise a rim or lip at its lower or bottom edge to prevent the bushing 120 from passing through the collar 118. The bushing 120 is preferably annular and may comprise an inner surface that has is part-spherical in cross-section. In an embodiment where the outer surface comprises a screw-thread, the bushing 120 may be sized such that the screw-thread on the outer surface interfaces with a complementary screw-thread lining the interior of the collar 118.

In one embodiment, placement of the fasteners through the bores 140 and collars 118 of the plate 110 permits a surgeon to accurately and securely place the plate 110 in its desired location and orientation, including as shown in FIGS. 1, 4, 5 10 and 12-14, so that the surgeon does not need to worry about movement of the adjacent bodies, movement of the components of the system, misalignment of the armatures 115 and associated collars 118, etc. In certain embodiments, the bores 140 may be tapered or chamfered to facilitate proper orientation and/or alignment of screws or other fasteners.

Each bushing 120, in turn, may comprise a substantially hollow opening for receiving a screw S2, as shown in FIGS. 2a-2b. The bushing 120 may be oriented in each collar 118 so as to provide freedom of movement in the x, y and z directions, or dorsally or plantarly or medially, or a combination thereof. The degree of freedom is determined by the orientation of the bushing 120 within the collar 118, which may be configured with increased or decreased tolerances (relative to the bushings) to increase or decrease the degree of freedom in orienting the bushings 120 and thereby the screws S2. The freedom of movement described above enables the screw S2 to rotate relative to the longitudinal plane of the plate 110 by up to 30 degrees of neutral in either side, therefore providing a total arc of 60 degrees.

Bushing 120 may further comprise an outwardly-extending protrusion or "key" 122 that protrudes radially from the outer surface of the bushing 120. The key 122 is preferably sized complementary to a notch 112 in the interior hollow surface of collar 118, as depicted in FIGS. 2a-2b. The key 122 is preferably on a proximal end of the bushing 120 (relative to the user) so that the key 122 cannot engage the notch 112 until the bushing 120 is received by and retained by the collar 118. The engagement of the key 122 with the notch 112 prevents further rotation and preferably movement of the bushing 120 relative to the collar 118, as described in greater detail below.

Still referring to FIG. 2, a tool 150 may be used to position a screw S2 through the bushing 120 and collar 118 in a desired trajectory/orientation as described herein. Due to the close tolerances of the collar 118 and the bushing 120, and the bottom rim of the collar 118 described above, the bushing 120 may not pass through the collar 118 even when not engaged with the collar 118 in a threaded engagement. The collar 118 may alternatively be tapered, and it is to be expressly understood that other means of providing a stop for the bushing 120 relative to the collar 118 are contemplated. The screw S2 may also comprise a threaded head 130, which may be received within the bushing 120 including by way of a threaded engagement.

Advancement of the screw within the bushing 120 (when placed within the collar 118) may be achieved by tool 150 without disturbing the bushing 120, as the shaft of the screws S2 is preferably narrower than the interior dimension of the bushing 120. However, further advancement of the screw S2 that causes threaded engagement with bushing 120 will result in rotation of the bushing 120, and ultimately engagement of the key 122 in the notch 112 of the collar 118. Engagement of the key 122 in notch 112 prevents further rotation of the bushing 120 and thereby locks the bushing 120 relative to the collar 118. This locking engagement is depicted in FIGS. 2a-2b. Any of the components described in this section may be provided with a high-friction surface to facilitate this locking of the bushing 120 relative to the collar 120. Thus, in use, the screw S2 may be threaded into the bushing until it reaches a limit of travel, whereupon further rotation of the screw S2 also rotates the bushing 120 causing the radially extending key 122 to translate rotationally so as to engage with the notch 112.

Alternatively, the bushing 120 may comprise a groove for receiving an anti-rotation element. The anti-rotation element of this embodiment may comprise a key for engaging with the notch of the collar, as described above, rather than the bushing itself. Upon insertion of the screw, the initial threaded portion passes through the bushing from the upper side of the plate and into the underlying bodies. The threaded screw head then begins to engage with the internal thread of the bushing. As the thread advances, the friction begins to rotate the bushing within the cavity. The anti-rotation element is engaged within the groove of the bushing, and is unable to rotate with the bushing once the key has engaged with the notch. Accordingly, the friction between these components and the engagement between the key and the notch create an interference frictional fit, thereby locking the assembly in a desired axial alignment. In embodiments, the anti-rotation element is circular and sized to be placed securely on an outer circumference of the bushing and within a groove in the bushing. The groove does not necessarily extend about an entire perimeter of the bushing. In other embodiments, the anti-rotation element is substantially in the shape of a "C." The anti-rotation element may be selectively removed from the bushing if desired, thereby changing the assembly from a locking type to a non-locking type. Alternatively, the key described herein may be selectively retractable relative to the anti-rotation element, thereby permitting the assembly to change from a locking to a non-locking type without deviating from the other aspects of the assembly described herein.

In yet another alternative embodiment, the bushing may be provided with no threading in the hole, the hole having a tapered configuration, and a screw may be provided with a tapered section for cooperation with this tapered hole in the bushing. Provided a force is applied in the axial direction which drives the tapered section of the screw into the tapered section of the bushing, rotation of the screw will result in rotation of the bushing and the locking mechanism of the polyaxial assembly will activate. Such a force may for example be applied in the instance that the screw has a lower section which is screwed into a substrate, resulting in a force which pulls the upper tapered section of the screw into the tapered hole of the bushing.

Thus, in embodiments, the inner surface of the recess is configured to taper from a proximal surface of the plate, relative to the user, to a distal surface of the plate. A bushing may be secured within the tapered recess by a frictional or interference fit between the bushing and the recess after being advanced within the recess by a predetermined distance. In embodiments, the bushing is permitted to pivot while retained by the recess, prior to being secured. This in turn allows the screw orientation to be adjusted relative to the plate.

As shown in FIG. 1, the plate 110 is configured to be positioned dorsally, in one placement of the system, while the armatures extend away and downwardly from the central portion of the plate 110 such that the inside surfaces of the collars 118 are oriented in a generally facing direction relative to the adjacent bodies or bone segments. This configuration in turn permits screws or other fasteners to be inserted in a converging but complementary manner, and without risk of intersecting one another. This configuration also permits screws or other fasteners (S1, S2) to be oriented in multiple orthogonal planes, while also permitting converging trajectories, thereby greatly improving compression, strength and simultaneously avoiding subsidence and undesired collision among the different fasteners.

The plates 110 described herein may further comprise one or more fenestrations 117, 119, which in certain embodiments are located and sized to accommodate 2 mm or other sized K-wires. The placement of K-wires and other temporary fasteners may be used to temporarily position and/or stabilize the plate 110 prior to insertion of permanent fasteners. The fenestrations may be different in size and/or shape to accommodate placement of other tools, implants, etc. In certain embodiments, no fenestrations are provided with the plate.

Any of the fasteners or screws referred to herein may be temporary or permanent during a fusion or other surgery practiced using the systems or methods described herein. Screws and other fasteners used with the systems and methods described herein may be locking or non-locking type. By way of example but not limitation, the screws S1 may be self-drilling, self-tapping poly-axial locking screws. The screws may be cortical or cancellous, however, as the diameter of the screw is increased, the resistance to fatigue and ultimately failure also increases. Therefore, cortical screws are preferred over cancellous screws. Alternatively, screws may have a larger than standard core diameter to account for this issue.

Any of the fasteners described herein may be used with or without pre-drilled holes in the underlying boney anatomy. In the embodiment where pre-drilled holes are employed, the diameter of the drill is preferably smaller than that of the core diameter of the screw such that insertion of the screw causes radial expansion and impaction of the surrounding bone. This in turn improves pull-out resistance. Furthermore, the fasteners may be inserted through the bores 140 and/or collars 118 by only making very small incisions, and in embodiments described herein may be performed via MIS procedures.

In embodiments, the system may be referred to as an orthopedic implant system. The system preferably comprises a central portion or spanning link having a longitudinal axis in the x direction. The spanning link is configured to receive at least one fastener. The fastener received by the spanning link preferably has an axis which forms an angle relative to the spanning link's longitudinal axis in the range of 80 degrees to 100 degrees. The spanning link may comprise a first leg link extending away in the y and z direction (as taken from the longitudinal axis in the x direction), which has an aperture for receiving, for example, another fastener. This fastener preferably has an axis that extends away from the first leg link fastener aperture in the direction of but not intersecting the axis of the fastener received by the spanning link. In one embodiment, the first leg link extends away in both the y and z direction to form a curve that defines at least 60 degrees of an arc.

The system may also be described as an orthopedic implant system which comprises a framework, scaffold or cage construct comprised of contiguous metal link portions that together have an outline which is a modified I-shape, U-shape or T-shape. The sole member of the I-shape or the center portion of the U-shape or T-shape comprises a metal spanning link, which may have a rectangular or modified rectangular outline which is preferably 4-20 times as long as it is wide and 1.5-3 times as wide as it is thick, and has a longitudinal axis in the x-direction (coinciding with the direction of a compression slot) and with a length that is between 15 and 60 mm, a width of from 2-5 mm and a thickness from 1-2.5 mm. This central link is strap-like in its proportions, and has nominally orthogonal and curved linkages or leg or arms links, which are also referred to as armatures. Together these linkages form a framework with one or both long sides of the metal spanning link. Near one or preferably both ends the spanning link has a fastener with an orthogonal axis in the z direction. This could comprise a staple leg but preferably comprises the combination of one or two spaced spanning link fastener apertures which each receive a fastener, which is preferably a screw, and further which is preferably threaded along its axis and on the outside of its torque driving head so as to form a locking fastener which mates with internal threads on the inside of the spanning fink fastener apertures. The area between the spanning link fastener apertures forms an area, i.e., the "fusion area" that overlies in use the fusion area on the associated bone segments. The plate further includes "outside" surfaces which face away from the associated bone in use and generally corresponding "inside" surfaces which face toward the associated bone in use and where edge surfaces join the inside and outside surfaces. The inside surfaces may include a curvature, for example, across the width of the plate, to accommodate the surface of the associated bone, or may be include at least in part, planar surfaces where the planar versions may have less rigidity and a greater ability to deflect and the radiused versions may be stiffer at the same volume of material.

The spanning link fasteners extend in the z-direction at angle of from 90° to 100° (+/−10°) with the longitudinal axis of the spanning link. As discussed, the spanning link has a central "fusion area" between two terminal spanning link fasteners which overlays an area of two bone segments for the purpose of promoting bone fusion. Spaced apart from each other, and optimally aligned with the spanning link apertures in the x or y direction, the construct also includes two leg links which nominally have the same width and thickness as the spanning link but which are shorter in length by 5-15 mm and that each extend away in the z direction from the of the spanning link longitudinal axis in a curve that optimally forms a portion of an arc. The curve can be a compound curve and also curve in the y direction. The arc is at least 45°, and preferably one leg forms a curve of 60°+/−10° and the other leg is longer and forms a curve of 90°+/−10°.

The leg links each include eyelets that have apertures for leg link fasteners and the apertures or surrounding internal surfaces of the eyelets define planes which are at an angle of 25° to 90° to the tangential surface of the attached leg link at a medial line of the leg link, and also at an angle of 10° to 60° to the longitudinal axis of the spanning link. The leg link fasteners are preferably polyaxial locking screws with a large degree of polyaxial freedom, such as 45° or even 60° (each)+/−10° of conical freedom prior to locking. In other embodiments, the polyaxial screws are non-locking type. One means of achieving this degree of pre-locked variability is with the use of a collar and/or bushing as described above. These fasteners each have an axis that extends back toward the longitudinal axis of the spanning member or into the fusion area. The axes are not in the same plane, but do extend or "converge" toward each other, and in fact, may even cross. One or both of the screws may be only partially threaded to cause compression across the fusion area and so as encircle the associated bone segments after implantation and cause a stable construct with compression at the fusion site where the bone segments meet. The present invention is specifically designed to promote this fusion by providing 3-dimensional fixation wrapping around the area of fusion and creating a stable position including compression at the fusion site.

Thus, the construct of the present invention provides a framework having a central link associated with a pair of perpendicular screws)(+/−10° which are spaced apart to form a fusion area therebetween and the central link further includes a pair of perpendicular leg links)(+/−10° that curve away from the central link and which each include an aperture that has a mating leg link screw where the two leg link screws angle back toward or into the fusion area so as to form an x-shape but wherein the screws do not interfere with each other. The construct has a minimal amount of metal for the degree of stability, and the minimal material provided allows for a certain degree of flexion in the central link and any associated arm or leg linking members. Thus, the construct achieves tri-planar orthogonal fixation in the plane of the central link, the plane of the central link fasteners and either across the fusion site or at the planes of the eyelets or the planes defined at the cross screws. Preferably one or both of the cross screws are partially threaded to provide for cross compression into the eyelet surfaces and in opposition to the central link fasteners.

In certain embodiments, the first leg link aperture defines a plane which is not parallel to the spanning link's longitudinal axis. In yet another embodiment, the implant system comprises a second leg link extending away from the spanning link in the y-z direction and having a length that may be the same as or different from the first leg link length. The second leg link preferably has an aperture which receives a fastener, and that fastener has an axis that extends away from the second leg link fastener aperture. In a preferred embodiment, the second leg link fastener axis is in the direction of a desired area of fusion for a particular surgery. Also, the first leg link fastener axis and the second leg link fastener axis preferably converge toward each other, but do not intersect or otherwise cause interference between the two leg link fasteners.

In embodiments, the second leg link aperture defines a plane which is not parallel to the spanning link's longitudinal axis. In other embodiments, the first leg link defines an arc of more than 45 degrees relative to the spanning link's longitudinal axis. In still other embodiments, the first leg link defines an arc of more than 75 degrees relative to the spanning link's longitudinal axis.

The first leg link length and the second leg link length are not necessarily the same. In one embodiment, the spanning link has a length of 15 to 60 mm, a width of 2 to 5 mm, and a thickness of 1 to 2.5 mm, and the first leg link has a length of 8 to 20 mm extending from the first spanning link and a width of 2 of 5 mm and a thickness of 1 of 2.5 mm.

In embodiments, the first and second leg links are formed of a material to cause the leg links to flex in response to a force applied to the same. The first leg link or the second leg link may form an arc of at least 85 degrees in the z direction.

The fasteners described above preferably have at least 30 degrees of conical freedom about their axes, and in another embodiment have at least 40 degrees of conical freedom. The first and second leg link fasteners preferably cross one another, although in differing planes, to form an X-shape. However, even with the above-recited degrees of freedom, the two fasteners do not contact each other. One or more of the leg link fasteners may contact an extension of the spanning link and by received by the extension, such as the distal tip of a fastener being threaded into an aperture in the extension.

Figure 3:
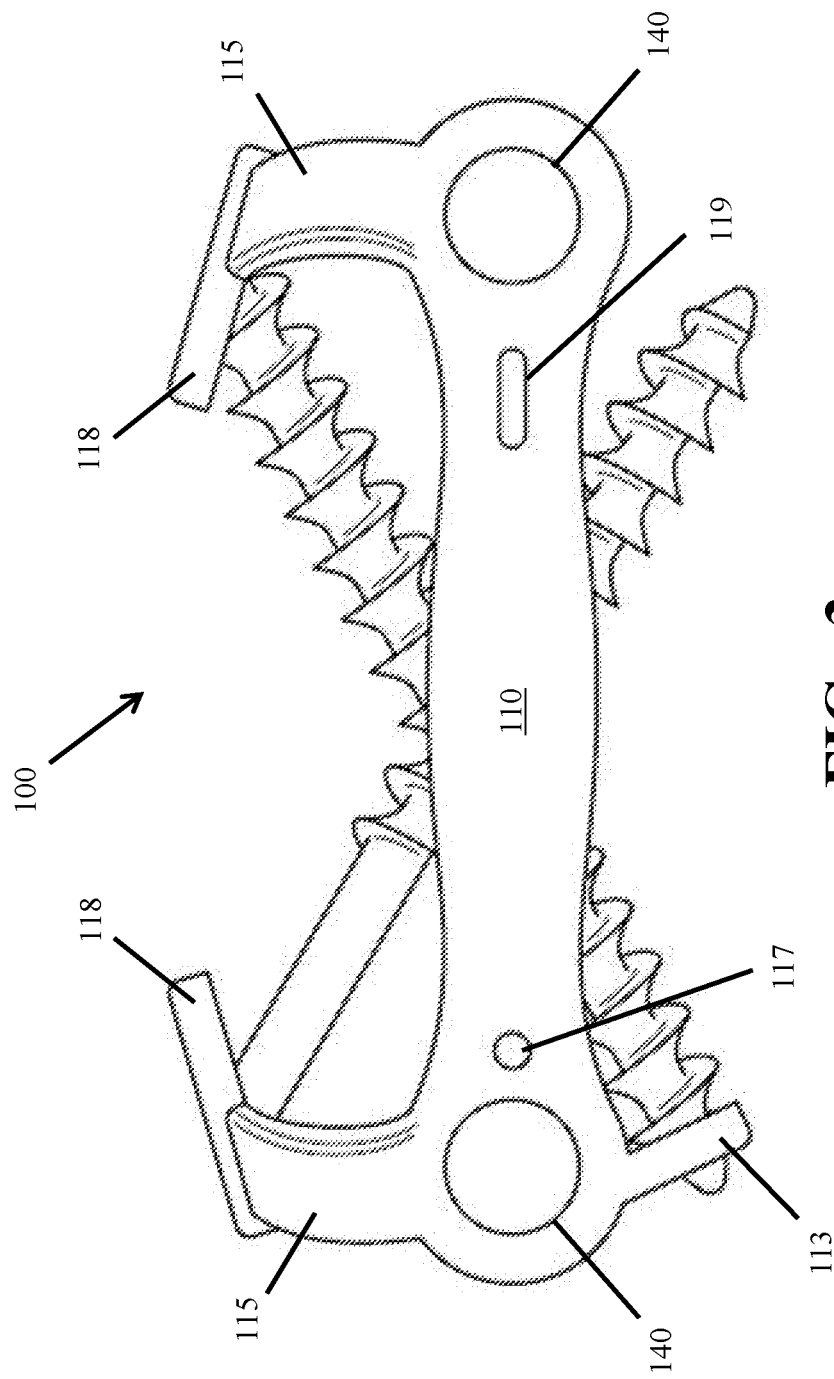
FIG. 3 shows a top plan view of the system according to another embodiment of the present disclosure.

In FIG. 3, an alternate embodiment of the present disclosure is shown in a top plan view. The plate 110 is similar to the ones described above, and the content relating to the plate of FIG. 2 is incorporated here by reference. The plate 110 of FIG. 3 comprises an extension 113 having an aperture for capturing the distal end of a screw S1 inserted through the opposite collar 118, as shown in FIG. 3. In this manner, the screw S1 can be captured and retained by the extension 113, which both provides rigidity of the screw S1 and prevents subsidence after implantation, and also ensures proper alignment of the screw S1 along a trajectory intersecting the aperture of the extension 113. The aperture is preferably threaded with a female thread to receive the threaded end of the screw S1. In this manner, the screw S1 passing through the aperture provides stability and rigidity, while the other screw S1 (which in a preferred embodiment is only partially threaded) is configured to provide compression through introduction in the underlying boney anatomy.

Figure 4:
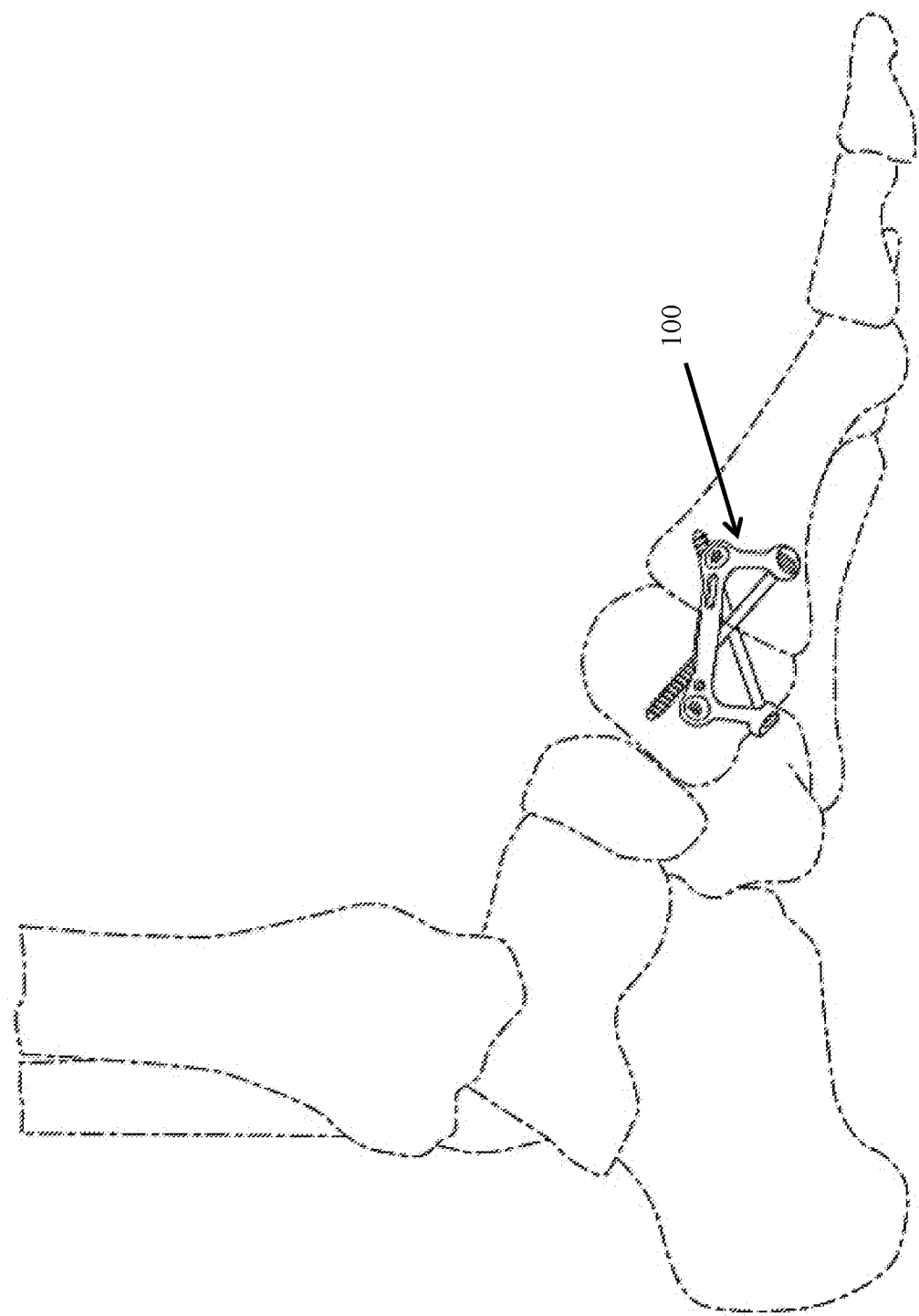
FIG. 4 shows a side perspective view of the system according to yet another embodiment of the present disclosure.
Figure 5:
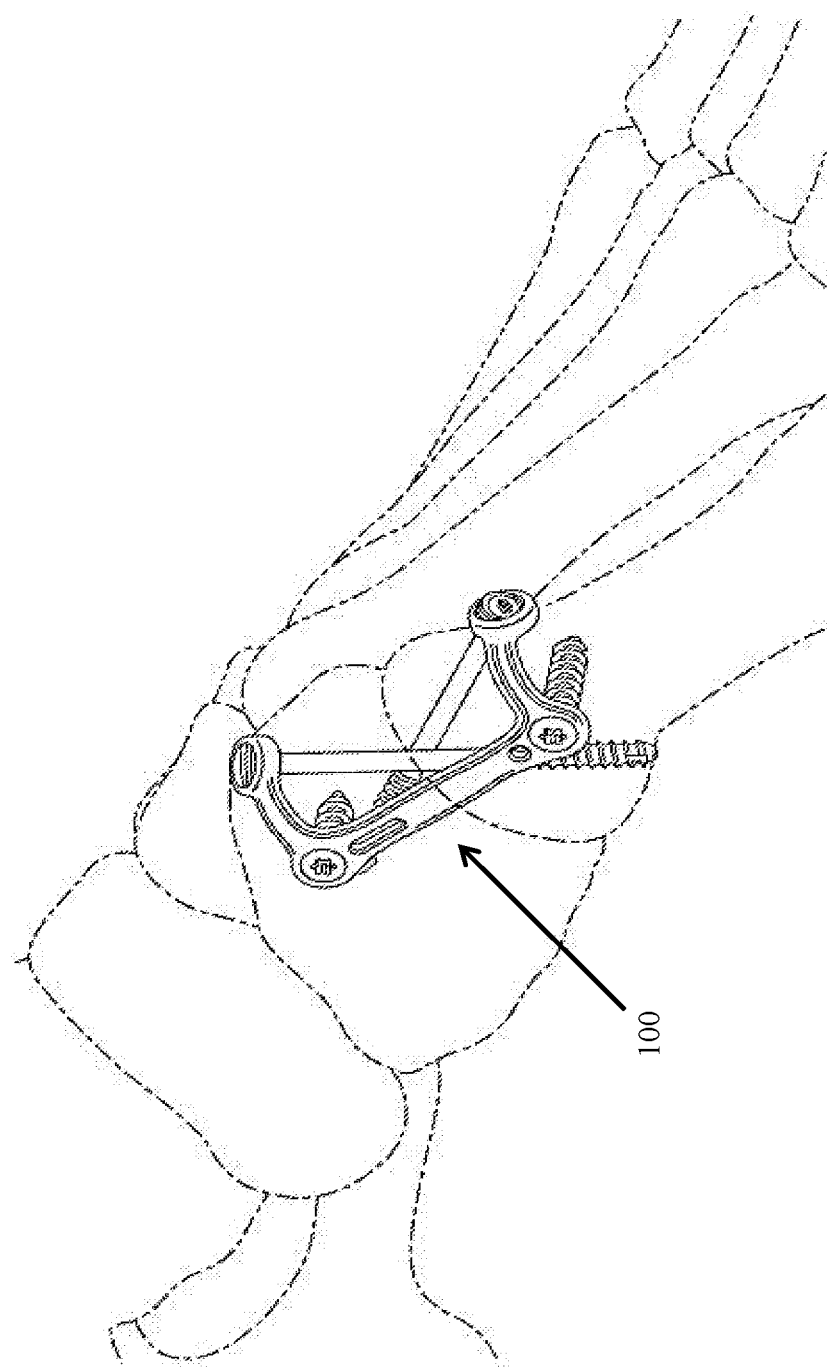
FIG. 5 shows another side perspective view of the system according to yet another embodiment of the present disclosure.

Referring now to FIG. 4, one particular orientation of the plate and fasteners described above is shown. In this arrangement, the plate 110 is positioned to address a Lapidus indication, whereby the armatures and terminating collars are positioned plantarly. Here, the primary fasteners are inserted through the collars of the armatures in a crossing but non-intersecting manner to facilitate a fusion of the first TMT joint, such as in a Lapidus procedure. FIG. 5 illustrates another orientation for facilitating a Lapidus procedure, wherein the armatures and collars are positioned dorsally. The system may be positioned in other manners than shown in FIGS. 4-5 while still achieving the benefits described above, including in other fusion and non-fusion surgical procedures, for example, for use in trauma-related procedures.

In one embodiment, the fasteners are prohibited from contacting one another, but nonetheless converge to pass close to one another to achieve the greatest possible compressive strength when coupled to the plate. Furthermore, the fasteners may be desirably oriented relative to the z-axis so as to avoid the fasteners passing only partially through the dense area of the adjacent bodies where subsidence is less likely to occur, and also to avoid gapping in certain areas of the joint. Secondary fasteners may also be inserted through the bores in the plate without interfering with the primary fasteners. The placement of the plate is such that there is adequate boney anatomy for the fasteners to be inserted without penetrating the bodies, and without intersecting each other.

The armatures may be oriented at more of a tangential angle relative to the central portion of the plate. This may permit placement of the plate more medially, or to conform more closely to the general shape of the adjacent bodies and thereby avoid discomfort to the patient.

Figure 6:
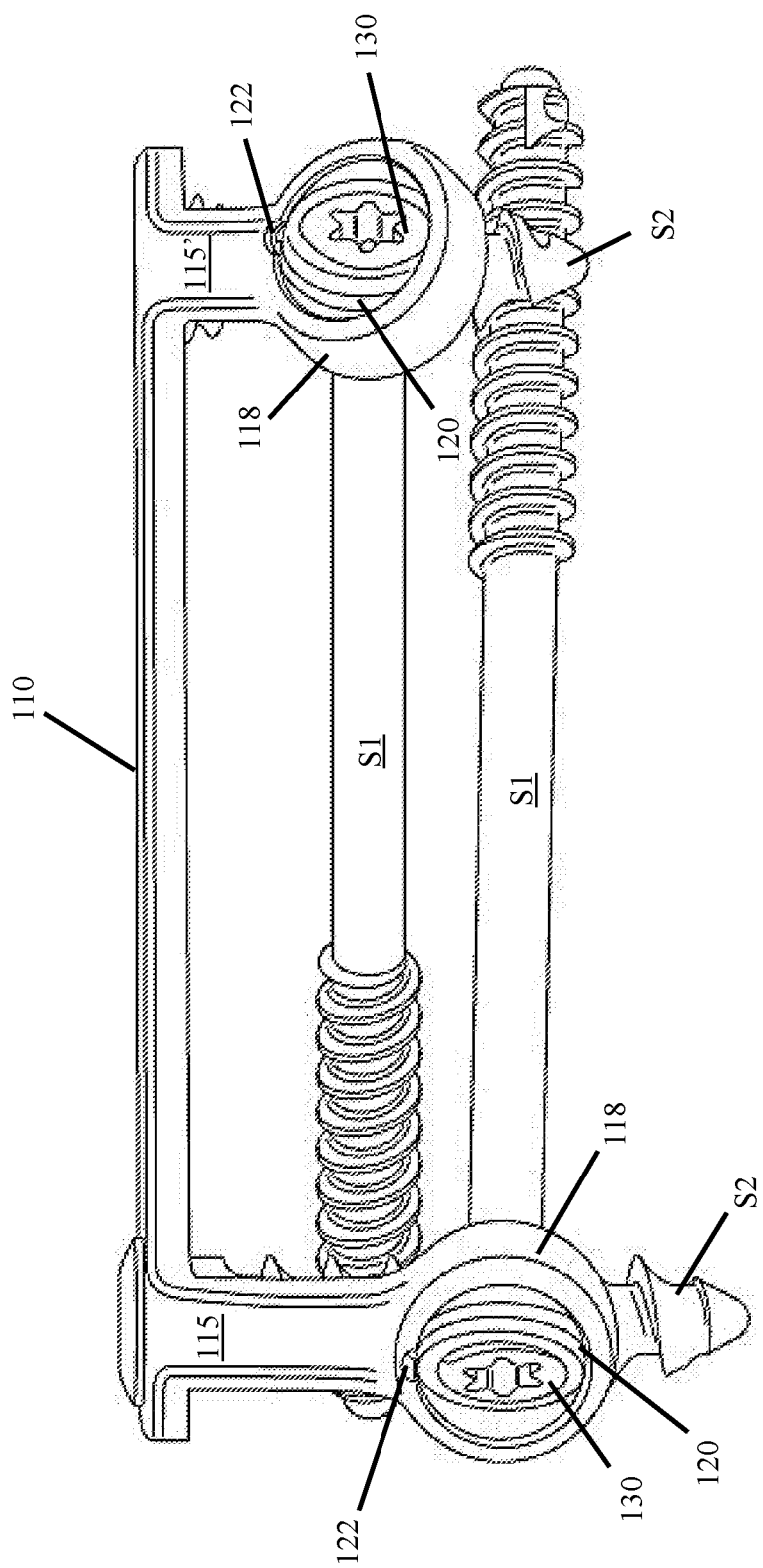
FIG. 6 shows a side elevation view of the system according to yet another embodiment of the present disclosure.
Figure 7:
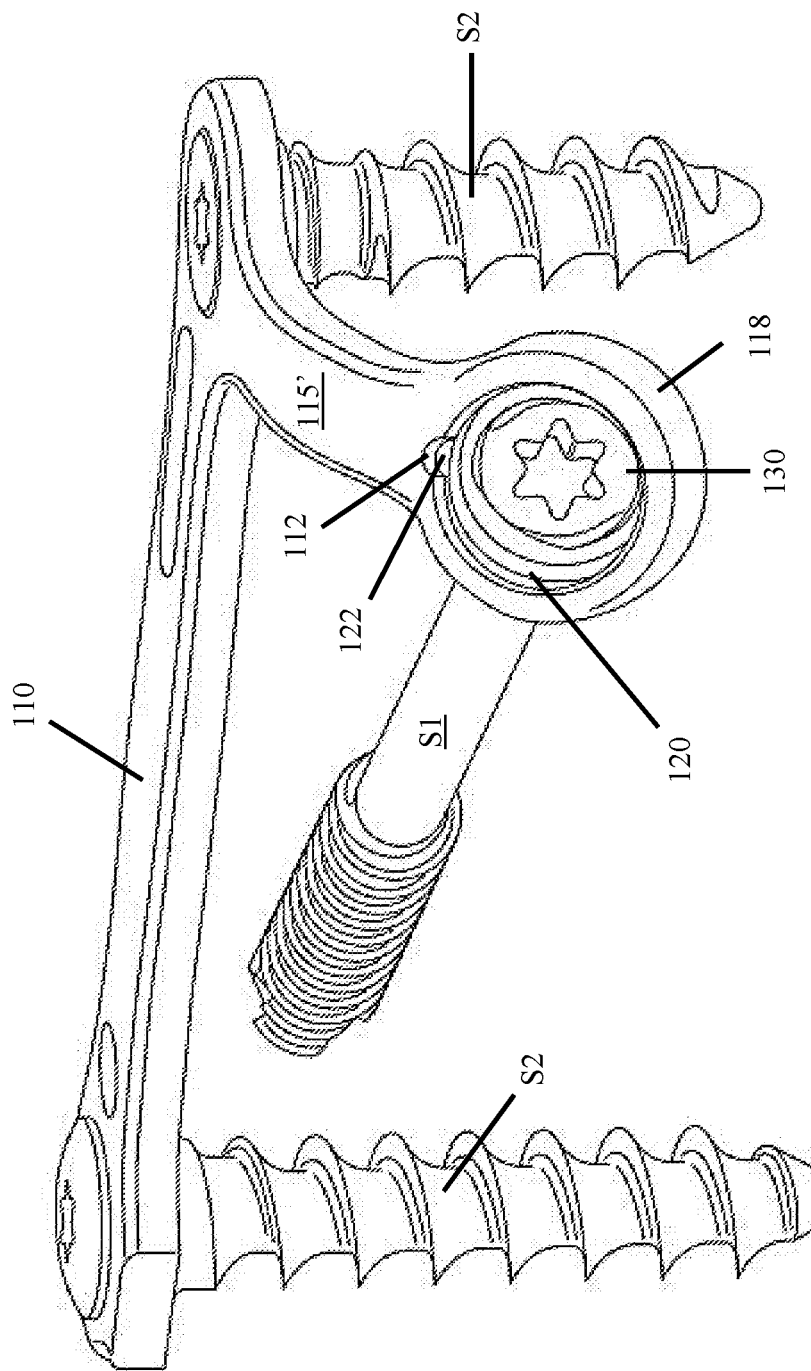
FIG. 7 shows a side perspective view of the system according to yet another embodiment of the present disclosure.

FIG. 6 shows a side elevation view of a system according to another embodiment. This view is particularly helpful in showing the multiple planes in which the fasteners are oriented, even more particularly how the fasteners may be positioned in three orthogonal planes to improve strength and resist movement. In this embodiment, the plate 110 comprises two differently sized armatures 115, 115' with one of the armatures 115' being shorter than the other 115. This permits the collar of the first armature 115' to be offset in the z-axis from the other collar of the longer armature 115. This system may be beneficial to ensure placement of fixations devices in multiple bodies at desired areas (i.e., bone density) or to further avoid collision of fasteners used in a relatively small area. FIG. 7 depicts another embodiment where only a single armature 115' is provided. The other aspects of the system described above apply equally to the components of these embodiments of FIGS. 6 and 7 and are incorporated herein by reference.

A person of ordinary skill in the art will recognize that the foregoing embodiments convey various manners of transmitting torque from a screw to a bushing so as to rotate the bushing and lock the bushing relative to a collar in which the bushing is placed. One of ordinary skill will appreciate that other means may be provided for this objective, and that the screw may be replaced with a bolt or equivalent component. In one alternate embodiment, the bushing may comprise a "slotted" upper surface to receive a flat-bladed or Phillips style screwdriver. One of ordinary skill will also appreciate that with the bushing in position within the collar of the armature, the bushing could then be rotated by means of a screwdriver until the key engages with the notch described above, so that the bushing locks in place in a desired orientation. Any screw or bolt or other item may then be attached to the bushing or driven through it with its axis in a particular desired orientation as then defined by the locked-in position of the bushing.

According to various embodiments described herein, the apertures for receiving primary fasteners (i.e., screws) are offset from the central portion of the compression plate. The offset nature of the apertures and the position of the armatures relative to the central portion of the plate provides for a more optimal placement and orientation of the fasteners relative to the joint. This is especially true when inserting the fasteners in a small area, in a difficult location or in a MIS application.

Figure 8:
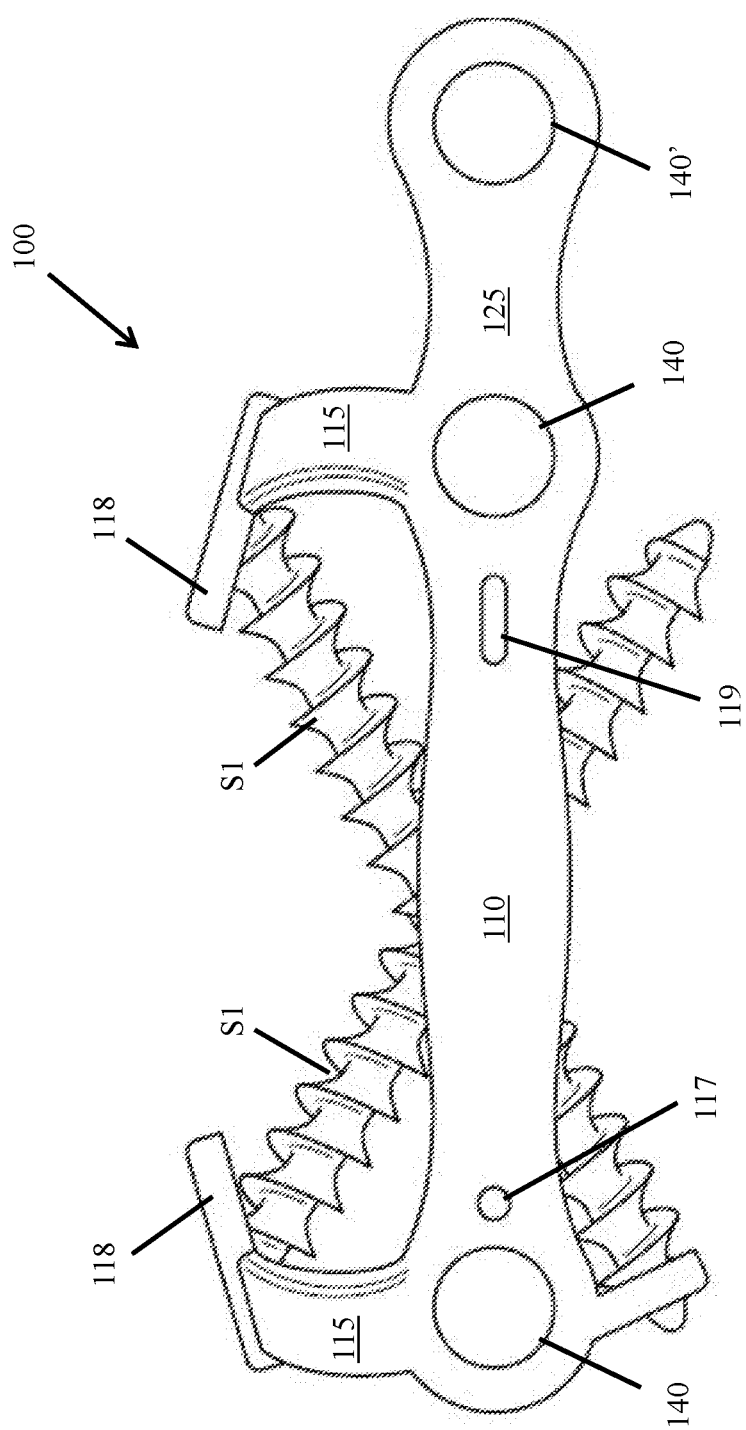
FIG. 8 shows a top plan view of the system according to yet another embodiment of the present disclosure.

Referring now to FIG. 8, another embodiment of the present disclosure is shown. Here, the plate 110 comprises an extension 125 that includes an additional bore 140'. This additional bore 140' facilitates placement of an additional fastener, thereby strengthening the connection between the plate and the underlying bodies. In this embodiment, one of the screws S1 may be captured as described above in relation to FIG. 3, although in other embodiments the screws S1 are not captured as shown in FIG. 2.

Figure 9:
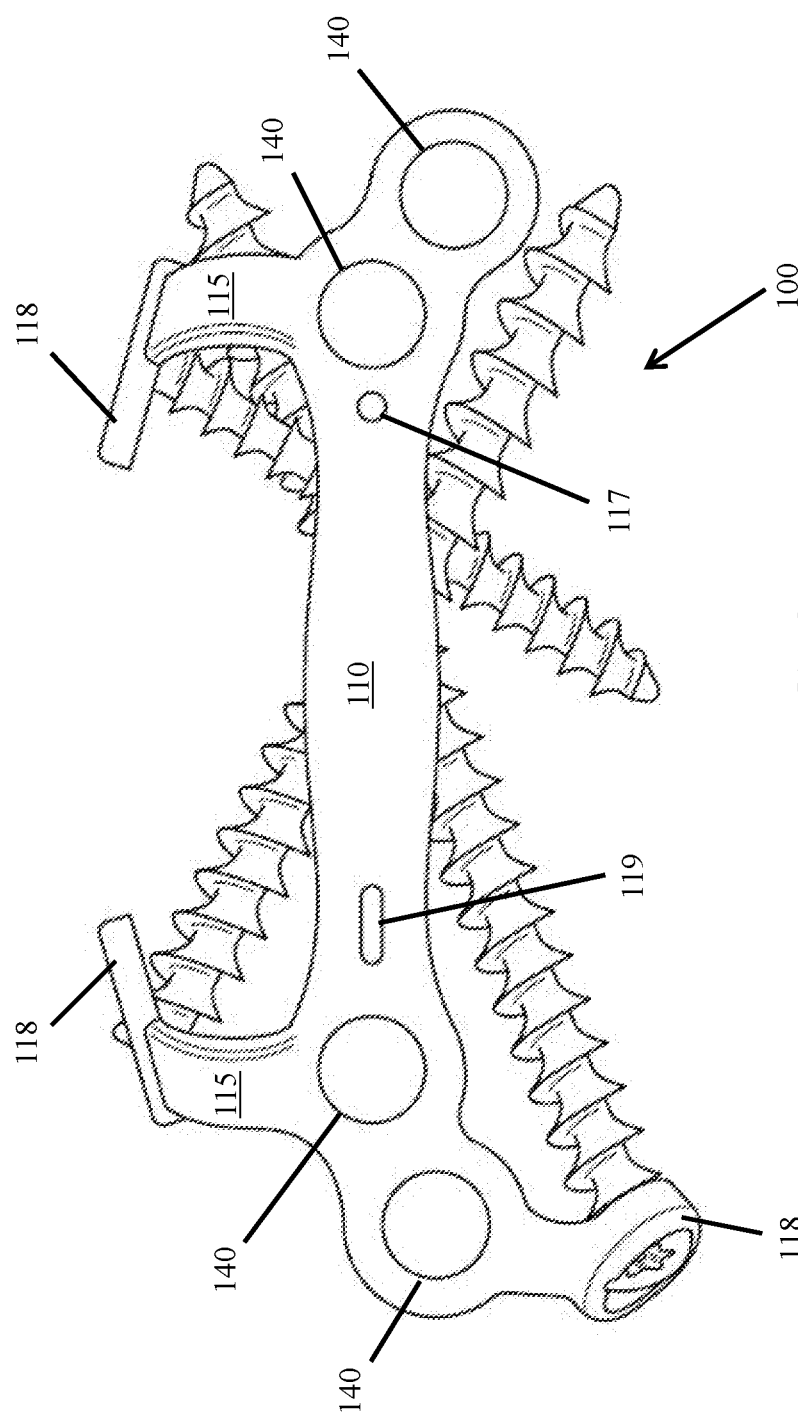
FIG. 9 shows another top plan view of the system according to yet another embodiment of the present disclosure.

A greater or fewer number of bores and/or fenestrations may be provided without departing from the inventive concepts described herein. For example, FIG. 9 depicts a modified plate 110 that comprises four bores 140. In addition, this plate 110 also comprises a third armature for placement of an additional screw. Variations on the embodiments of FIGS. 8 and 9 are contemplated and considered within the scope of the present disclosure. It is particularly useful for the plate to include a compression slot especially aligned with the longitudinal axis of the plate, and which is of a width only sufficient to receive a k-wire in diameter and which is longer than it is wide so that a first bone segment may be moved relative to a second bone segment by repositioning the k-wire in the slot.

Figure 10:
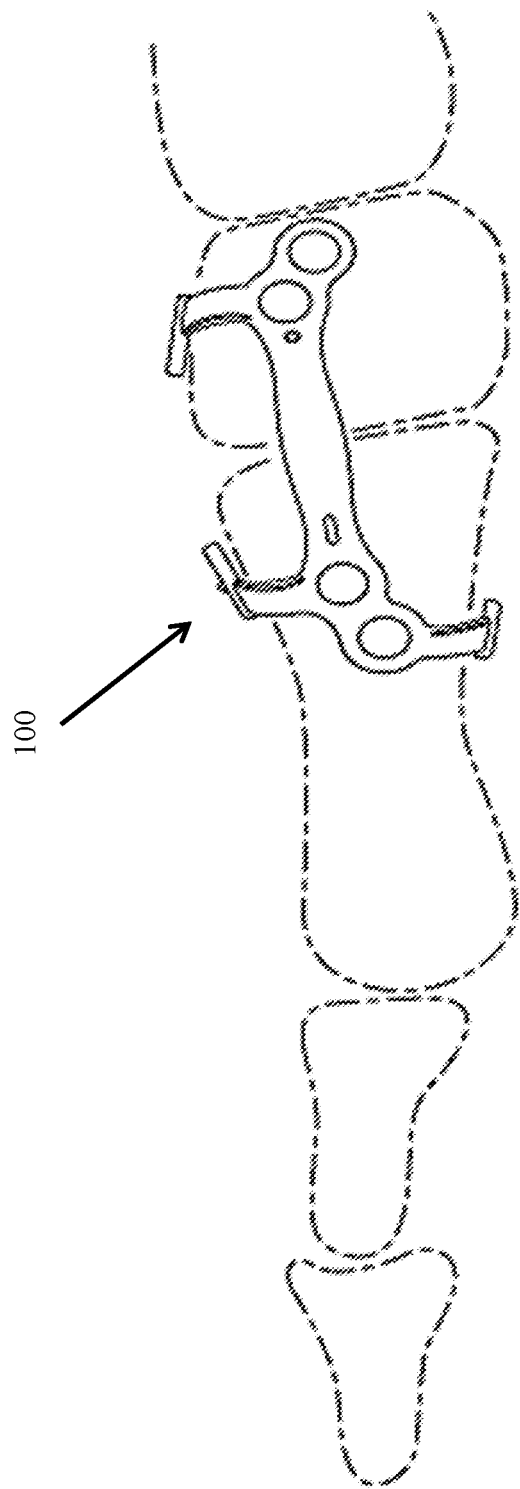
FIG. 10 shows a side perspective view of the system of FIG. 9.

FIG. 10 shows the system of FIG. 9 positioned against the underlying boney anatomy. In this manner, the guide may be useful in a MTP fusion, and further beneficial in the sense the plate provides both dorsal and plantar-positioned collars for introducing fixations devices into the bodies, further assuring solid compression and avoiding gapping.

Figure 11:
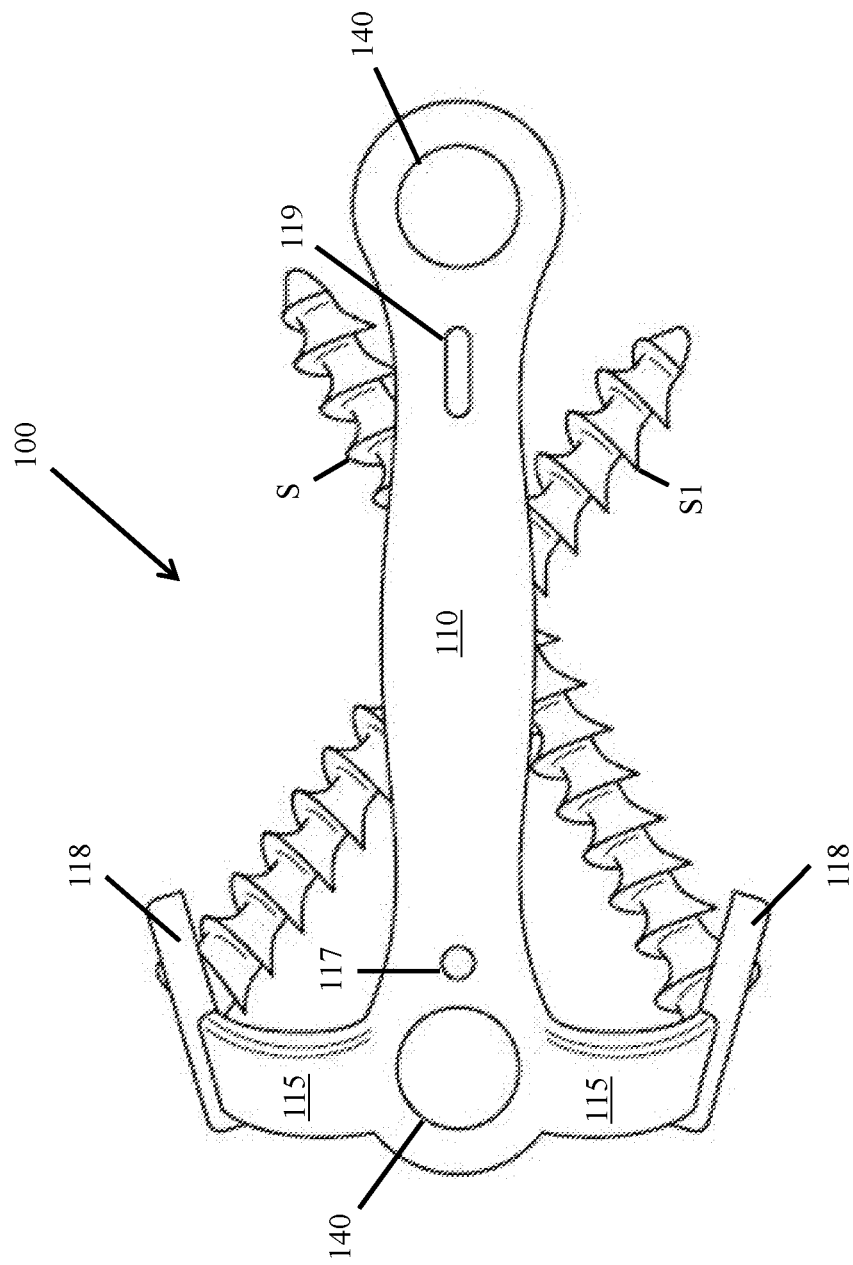
FIG. 11 shows a top plan view of the system according to yet another embodiment of the present disclosure.
Figure 12:
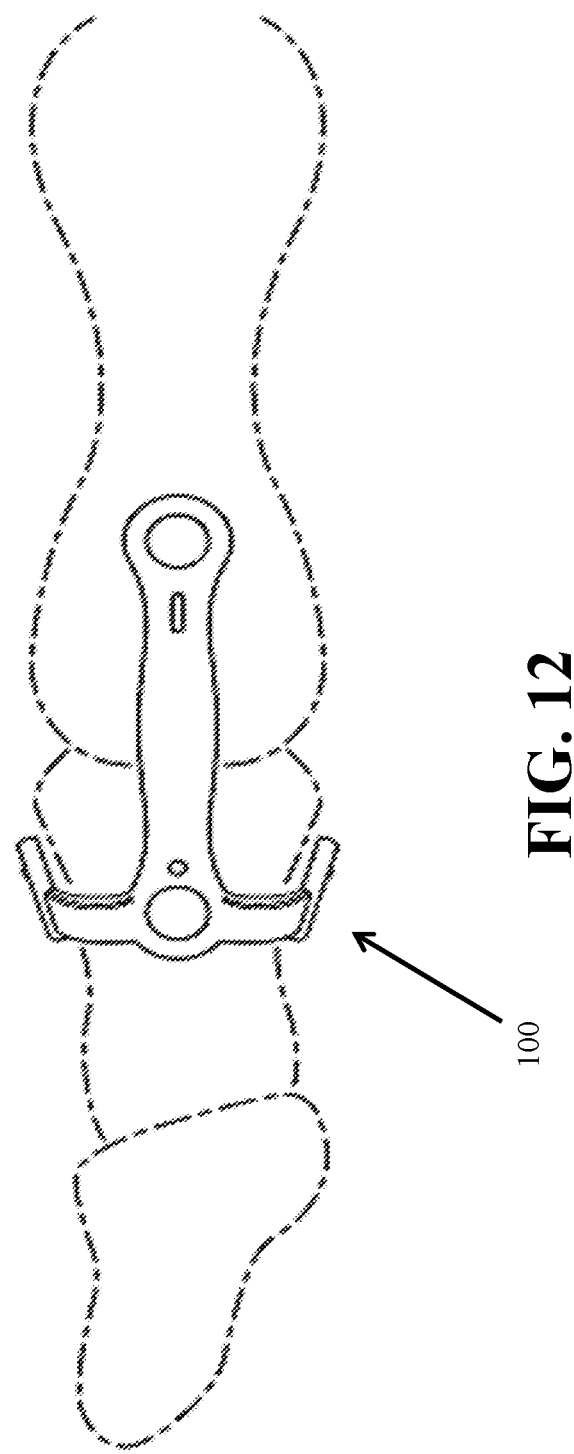
FIG. 12 shows a side elevation view of the system of FIG. 11.

FIG. 11 shows a plate 110 having armatures 115 only about one longitudinal end of the central portion of the plate 110. This configuration is particularly beneficial when addressing Lapidus indications. The screws S1 may be retained by any of the bushings described above, including with the anti-rotation element. Accordingly, applicant incorporates those paragraphs of the Detailed Description herein by reference. FIG. 12 is the system of FIG. 11 shown with the underlying bodies, which may be used in a Lapidus surgery as described above in relation to FIG. 4.

According to embodiments, the armatures may reach from 60 to 120 degrees in range, unlike many plates that permit only 90 degree orientations. This is particularly beneficial for procedures on the foot and ankle, where degrees of freedom and corresponding flexibility allow a surgeon to perform procedures that are not permissible with current state of the art plate and screw systems. It is to be expressly understood that the plate and armatures described herein may be curved or angled to conform closely to the surrounding patient anatomy. The material of the plate and other components of the systems described herein may comprise stainless steel, titanium, titanium alloy, aluminum alloy, chromium alloy, vanadium and other metals or metal alloys. The components may further comprise PEEK, carbon fiber, polyurethane, polyethylene, ABS plastics, photo-polymers, resins, fiber-encased resinous materials, rubber, latex, synthetic rubber, synthetic materials, polymers, and natural materials.

Figure 13:
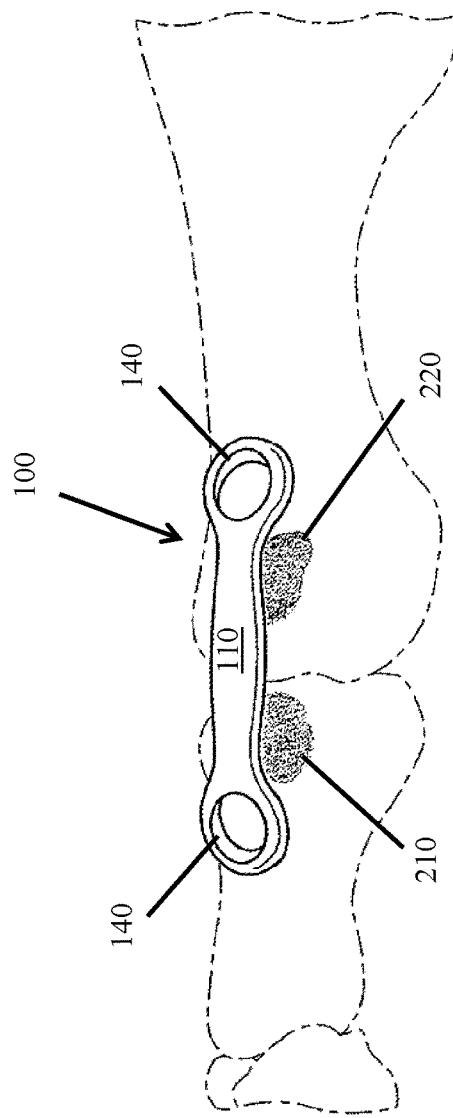
FIG. 13 shows a perspective view of particular method steps according to an embodiment of the present disclosure.

Referring now to FIG. 13, an embodiment is shown where the central portion of the plate does not include extensions or armatures. This type of component may be particularly desirable for use in MIS applications. The general benefits of the system and methods described above in the Summary and Detailed Description are still achieved with this particular embodiment.

In FIG. 13, the plate 110 has been slightly elevated from the underlying anatomy to illustrate how adjacent bodies may be prepared in advance by a surgeon to achieve even greater alignment and compression when installing the system in its varying embodiments. For instance, the boney anatomy may be cut, drilled or debrided 210, 220 to allow opposite ends of the plate and the corresponding bores 140 to rest congruently along the surfaces removed by the surgeon. This site preparation may be quickly and easily performed and assist in placement of the components of the system described herein.

The preparation by cutting, drilling or debriding 210, 220 described above may also be performed in a manner so that any armatures associated with the plate 110 are required to deflect slightly in order to be positioned on the adjacent bodies, thereby creating an interference fit or snap-fit. The frictional engagement may also help increase compressive strength of the plate 110. However, it is not necessary to perform preparation of the surgical site in order to utilize the benefits of the system and methods described herein.

Figure 14:
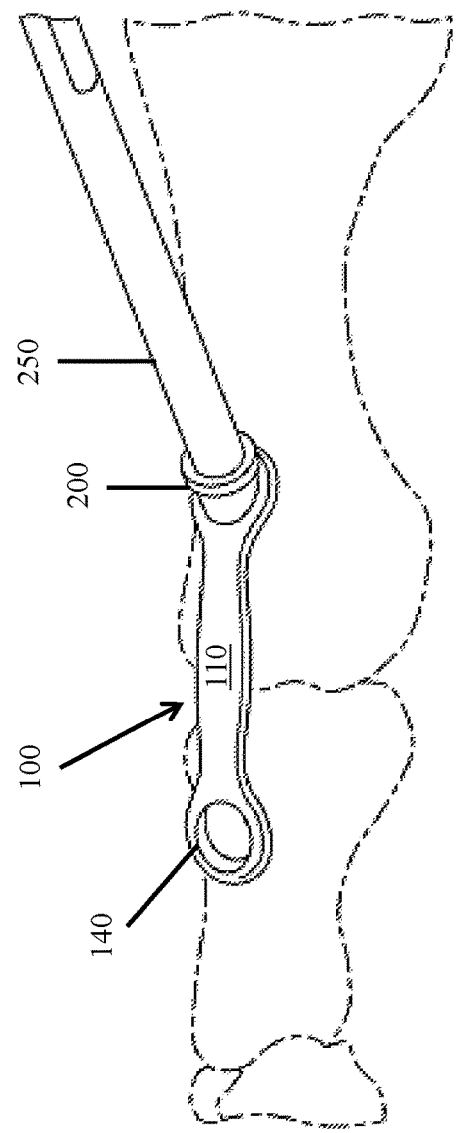
FIG. 14 shows a perspective view of an additional method step according to an embodiment of the present disclosure.

Methods of performing procedures using the aforementioned system are also within the scope of the present disclosure. Referring now to FIGS. 13-14, various stages or steps of the system being used in a surgical setting are shown. Although depicted relative to a foot joint, it is expressly understood that other joints and other adjacent bodies may employ the following systems and methods with equal efficacy. In FIG. 13, the plate 110 is shown positioned next to the adjacent bodies where compression is needed to ensure a successful fusion, to use one example. The plate 110 may be positioned without secondary fasteners and in a location where the plate 110 spans the joint between the adjacent bodies. The bodies may have been prepared in advance, such as by cutting or otherwise removing the surfaces (as described above) that would otherwise interfere with placement of the compression plate. In FIG. 14, an insertion instrument 250 is shown being inserted through one of the bores 140. Other instruments may comprise any of those known to a person of ordinary skill in the art for cutting, drilling, debriding, shaving or removing boney anatomy.

According to one embodiment, the system and method may comprise the use of one or more inserts. The inserts, such as insert 200 shown in FIG. 14, may have surfaces that are adapted to receive a fastener such as a screw and enhance the plate's 110 ability to promote crossing but non-intersecting placement of the fasteners therethrough and, once inserted, ensures that the adjacent bodies are in compression and that the fasteners will not subside during the surgery and recovery by the patient.

Referring again to FIG. 14, inserts 200 may be placed within one or more bores 140 of the plate 110 and further direct the fasteners through the plate 110. These inserts 200 may extend outwardly from the proximal surface of the plate 110, may extend inwardly from the distal surface of the plate 110, or may be positioned substantially flush with the plate 110, depending on the surgeon's preference and the particular demands of the surgical procedure to be performed. In one embodiment, the boney anatomy of the patient may be prepared (as described above in FIG. 13) to allow a surgeon to countersink the inserts 200 into the adjacent bodies. In embodiments, the insert 200 comprises a cam, a slope or equivalently-shaped surface to provide a pre-determined orientation to a screw or equivalent fastener, relative to the plate 110 that receives the insert 200.

Figure 15B:
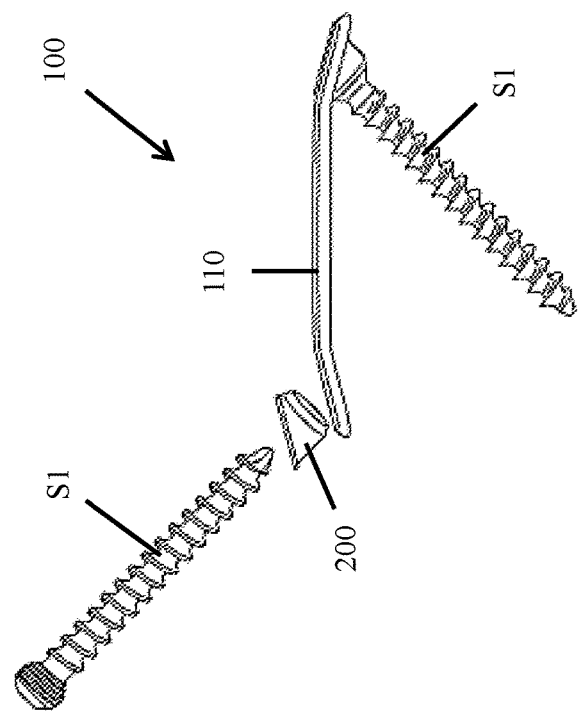
FIGS. 15A-15C show detailed perspective views of the system and method according to embodiments of the present disclosure.
Figure 15A:
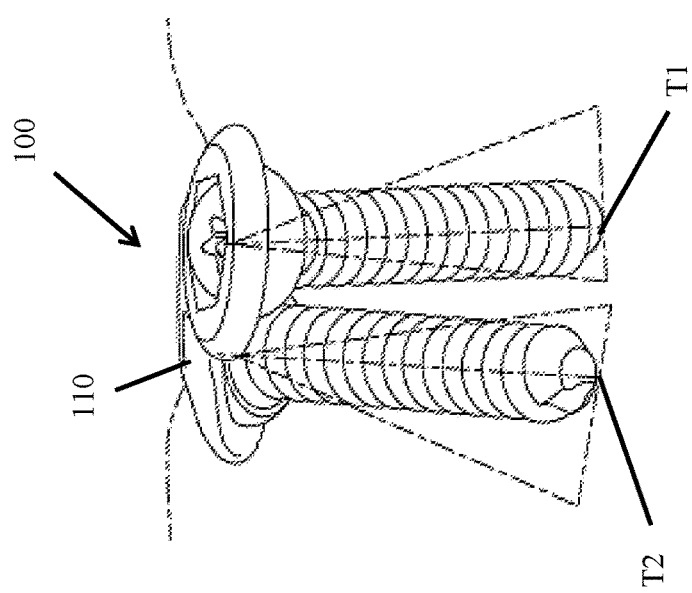
Figure 15C:
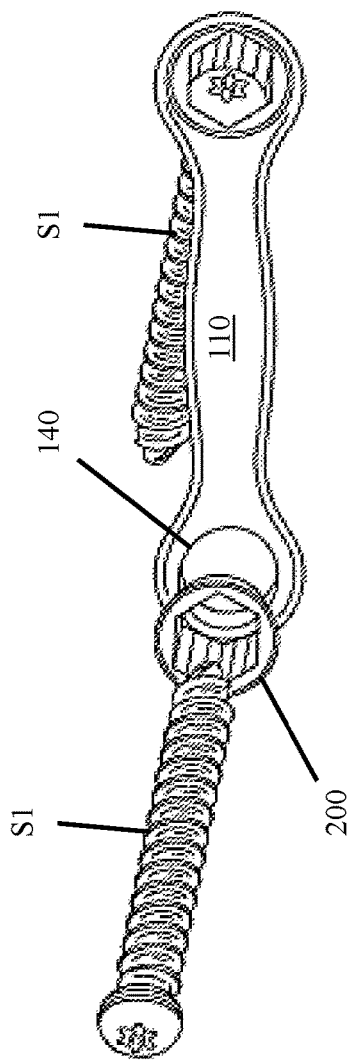

The inserts 200 further promote use of the compression plate in a MIS procedure. Further illustration of the aspects of this particular embodiment is provided in FIGS. 15B-C. It is to be understood that the system of FIGS. 15A-C is preferably for use in a MIS procedure. The plate of this embodiment has a central portion, and two armatures having recesses at their distal ends. As distinguished form the embodiment of FIG. 2, however, the armatures extend parallel to the longitudinal or x-axis of the plate's central portion. In this embodiment, the fasteners may still converge and cross one another, albeit in different planes so as not to contact one another. This may be achieved, for example, by the orientation of the apertures of the inserts, or by the orientation of the apertures in the first and second armatures.

FIG. 15A illustrates the unique placement of the fasteners once placed through the compression plate and its inserts. The trajectories T1, T2 of the fasteners are shown as converging but having complementary planes so that, while not permitted to contact one another, generally achieve the greatest degree of compression by virtue of their respective vectors. The close placement of the converging fasteners also reduces the chance of gapping and misalignment of the joint after the compression plate has been secured to the adjacent bodies. The range of allowable trajectories for each of the fasteners may be configured via a selection of various inserts, each of which features a different pre-defined orientation relative to the holes of the plate.

Figure 16:
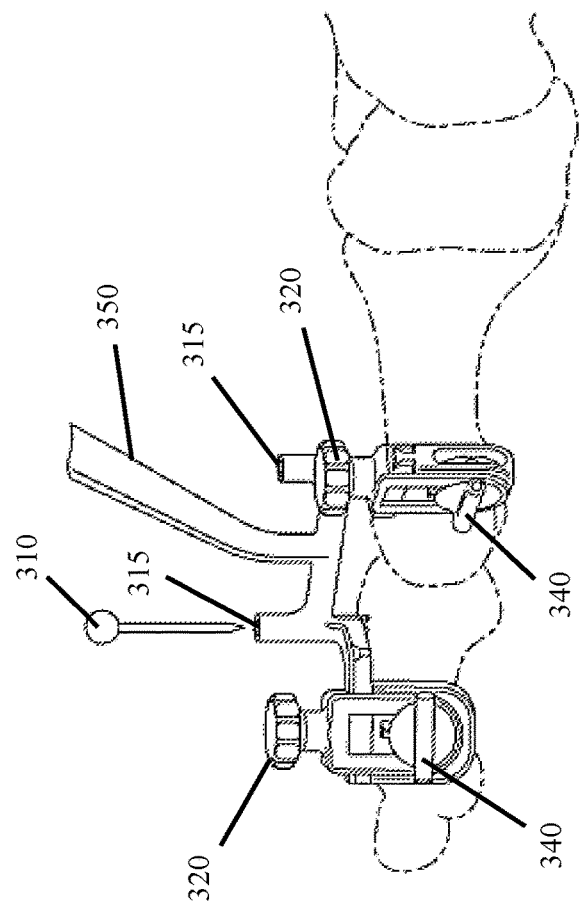
FIG. 16 shows a perspective view of an instrument for use with the systems and methods according to embodiments of the present disclosure.

FIG. 16 show a tool 350 according to one embodiment, which assists a surgeon in placement of a first and a second fastener through the plate. As shown, the tool 350 closely mimics the functionality of a jig, whereby the tool 350 permits registration via a primary fastener, or alternatively a temporary fastener 310. The tool 350 may comprise adjustable settings 320, 340 to lock the tool 350 in the precise location. The tool 350 is preferably adjustable in various dimensions, including by adjustment of the position of a first and a second alignment head 315 relative to the respective first and second apertures. Thus, an alignment head 315 may be positioned against any one fastener and then be adjusted to position the other alignment head 315 in the desired location for a second fastener. The alignment heads 315 provide the necessary alignment of the fasteners and may comprise indicia to facilitate the proper alignment. The use of multiple registration points allows a user to ensure that the tool is properly positioned before making adjustment to the adjustment heads. One or more of the registration points may be based upon a locking or non-locking fastener, a temporary or permanent fastener, or alternatively a segment of the plate or the inserts thereto. The tool 350 may also comprise a handle for positioning by the surgeon, and may comprise dials or gauges as depicted in FIG. 16.

Although specific aspects shown in these Figures are not expressly described, it should be understood that any of the features described above in connection with other embodiments apply equally to the embodiments of FIGS. 1-15C.

One having skill in the art will appreciate that embodiments of the present disclosure may have various sizes. The sizes of the various elements of embodiments of the present disclosure may be sized based on various factors including, for example, the anatomical variances of the patient, the person or other device operating with or otherwise using the components of the system, the surgical site location, physical attributes of the bodies and other anatomical features of a particular patient, and other dimensional variations including, for example, width, length and thickness, and the size of associated surgical tools or fasteners.

Any of the components described herein may be sized to only complement other components in a specific segment of the system, such as an insert being sized to only be received by a particular bore or collar of the system. Further, certain component(s) may comprise surface finishing, such as by electroplating, to imbue the components with coloring, shading, cross-hatching or other visually or tactile-observable features in order to aid identification of the component(s). Indicia may be included on the plate and/or segments of the plate to indicate a particular insert, screw, fastener, etc. to be used with that particular segment, or to indicate a sequence or order of performing various steps with the system described above. Indicia may also appear on an instrument or tool indicating which area of the system the particular instrument or tool is to be used, a direction for placing the instrument or tool, identifying a body or anatomical feature or landmark for accessing with the instrument or tool, etc.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. For example, certain geometries have been shown where an armature is on one medial side of a plate, but could be reversed and still provide the same benefits as described herein. Similarly, armatures and collars could be lengthened or shortened or substituted for extensions, as described above, without departing from the novel concepts captured by the appended claims.

The foregoing discussion of the disclosure has also been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment.

The present inventions, in various embodiments, include components, methods, processes, systems and/or apparatuses substantially as depicted and described herein, including various embodiments, subcombinations, and subsets thereof. Those of skill in the art will understand how to make and use the present inventions after understanding the present disclosure. The present inventions, in various embodiments, include providing devices and processes in the absence of items not depicted and/or described herein or in various embodiments hereof, including in the absence of such items as may have been used in previous devices or processes, e.g., for improving performance, achieving ease and/or reducing cost of implementation.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An orthopedic implant system, comprising:
a first plate fastener;
a second plate fastener;
a first armature fastener;
a second armature fastener;
a plate having a longitudinal axis in an x direction and having a first plate fastener aperture that receives the first plate fastener and a second plate fastener aperture that receives the second plate fastener, the plate defining a fusion area located between the first plate fastener and the second plate fastener;
a first armature extending away in an y-z direction having a first armature length from the plate longitudinal axis and a first armature fastener aperture that receives the first armature fastener that has a first armature fastener axis that extends away from the first armature fastener aperture in the direction of the fusion area;
a second armature extending away in the y-z direction having a second armature length from the plate longitudinal axis and having a second armature fastener aperture that receives the second armature fastener that has a second armature fastener axis that extends away from the second armature fastener aperture in the direction of the fusion area;
an extension stemming from the plate in a direction generally opposite the first armature, the extension having an extension armature configured to receive a distal end of the second armature fastener; and
wherein the first armature fastener axis and the second armature fastener axes converge, but do not intersect.

2. The orthopedic implant system as set forth in 1, wherein the first armature aperture defines a plane that is not parallel to the plate longitudinal axis.

3. The orthopedic implant system as set forth in 2, wherein the second armature aperture defines a plane that is not parallel to the plate longitudinal axis.

4. The orthopedic implant system as set forth in claim 2, wherein the first armature defines an arc of more than 45 degrees relative to the plate longitudinal axis.

5. The orthopedic implant system as set forth in claim 4, wherein the first armature defines an arc of more than 60 degrees relative to the plate longitudinal axis.

6. The orthopedic implant system as set forth in claim 5, wherein the first armature defines an arc of more than 75 degrees relative to the plate longitudinal axis.

7. The orthopedic implant of claim 5, wherein the first or the second armature are configured to flex in response to a force applied during implantation.

8. The orthopedic implant system as set forth in 1, wherein one or more of the first and second plate fasteners and the first and second armature fasteners is a locking fastener.

9. The orthopedic implant system as set forth in claim 1, wherein one or more of the first and second plate fasteners and the first and second armature fasteners is a polyaxial fastener.

10. The orthopedic implant system as set forth in claim 9, wherein one or more of the first and second plate fasteners and the first and second armature fastener is a locking fastener.

11. The orthopedic implant of claim 1, wherein the first plate fastener is a locking screw.

12. The orthopedic implant of claim 1, wherein at least one of the first the second armature fastener is a polyaxial screw.

13. The orthopedic implant of claim 1, wherein both of the first and the second armature fastener are a polyaxial screw.

14. The orthopedic implant of claim 12, wherein the polyaxial screw has at least 40 degrees of conical freedom.

15. The orthopedic implant of claim 1, wherein one of the first and the second armature fastener is only partially threaded to form a compression screw.

* * * * *